United States Patent [19]

Metzner

[11] Patent Number: 4,995,959

[45] Date of Patent: Feb. 26, 1991

[54] MEASURING APPARATUS FOR DETERMINATION OF THE ACTIVITY OR OF THE CONCENTRATION OF IONS IN SOLUTIONS

[75] Inventor: Klaus Metzner, Friedrichsdorf, Fed. Rep. of Germany

[73] Assignee: Fresenius, AG, Bad Homburg, Fed. Rep. of Germany

[21] Appl. No.: 410,123

[22] Filed: Sep. 20, 1989

[30] Foreign Application Priority Data

Sep. 24, 1988 [DE] Fed. Rep. of Germany ....... 3832528

[51] Int. Cl.$^5$ ............................................ G01N 27/27
[52] U.S. Cl. ...................................... 204/411; 204/409
[58] Field of Search ........................ 204/409, 411, 1 T

[56] References Cited

U.S. PATENT DOCUMENTS 4,797,191 1/1989 Metzner et al. ...................... 204/411

Primary Examiner—G. L. Kaplan
Attorney, Agent, or Firm—Omri M. Behr

[57] ABSTRACT

In a measuring device for determination of the activity or the concentration of ions in solution comprising a flow channel (24) having a reference electrode and at least one measuring electrode, said flow channel having a first end (22) and a second end (23); a first line (18) connecting said first end of said flow channel to at least one calibrating liquid container (1,2,3) through first valve means (5,6,7); a first pumping means (14A) interposed in said first line (18) between said first valve means (5,6,7) and said first end (22) of said flow channel (24); a discharge line (19) connected to said first line adjacent said first end (22) of said flow channel (24), said discharge line having second pumping means (14B); a sample feed line (25) connected to said second end (23) of said flow channel for providing a sample to said flow channel; first and second sensors (10,11) arranged in said first and second ends of said flow channel, respectively, for detecting the flowing fronts of liquids, said sensors being capable of discriminating between the presence and absence of liquids and control means coupled to said sensors, pumping means, and valve means for controlling said pumping means and valve means, the improvement comprising a connection line (21) branching off from said exit line (19) of said second pump (14B), said connection line exiting into said flow channel (24) in the vicinity of said first exit (23), said connecting line (21), being provided with a first valve (9) and in said exit line (19), between the juncture of said lines (18) and 19 at mixing point 27 and the point of connection of connection line (21) to said exit line (19), a second valve (8) being provided.

8 Claims, 2 Drawing Sheets

MEASURING APPARATUS FOR DETERMINATION OF THE ACTIVITY OR OF THE CONCENTRATION OF IONS IN SOLUTIONS

FIELD OF THE INVENTION

Measurement of activity or concentration of ions in solution.

BACKGROUND OF THE INVENTION

The invention is directed to a measuring arrangement for the determination of the activity or concentration of ions in solution which comprises at least one measuring electrode and a reference electrode with which are connected by a flow channel, provided with a first exit and a second exit, which is connected with at least one calibration container by means of a dosage line provide with a first pump and at least one valve, wherein said dosage line is further provided on exit line between said first pump and said flow channel in which there is provided a second pump. The test sample line measuring arrangement is connected with said flow channel.

An arrangement of the foregoing type is disclosed in DE-OS 3416956 (U.S. Pat. No. 4,797,191), the disclosure of which is incorporated herein by reference. This prior art device comprises an electrode unit (ion sensitive electrode and reference electrode) and a flow channel connected with this electrode unit. The first exit 23 of the flow channel is connected over a first line with the calibration solution containers, the exit is provided with a sampling guide line. In this first line, there is provided a pump which forwards the calibration solution to the electrode entity. From this first line, a discharge or waste line branches off to the discharge container. At both exits of the flow channel, downstream of the first pump, as well as in the discharge line, there are provided flow through sensors with which the fill level of the respective lines are tested. Downstream of the calibration container and before the discharge container, a blocking valve is provided. In the discharge line, there is provided a second pump which is suitably combined with the first pump to yield a double sided pump with two pumping segments. With such an arrangement as described above, the sample is measured and thereafter the calibration carried out. The electrodes must be washed before and after calibration in order to avoid errors due to residues of the sample or calibration fluid.

In order to carry out the washing of the flow channel, the calibration fluid is pumped by the pump through the second exit in the flow channel till this channel is completely filled. In this stage, test residues which were not entirely pumped out during the measuring step can be forced into the sample guide line and from there arrive in the suction aspiration cannula from which these sample residues could drip back into the sample container.

After the washing step, the calibration fluid is pumped off through the second exit in the flow channel and, via the discharge line, is discharged into the discharge container. There is no washing of the sample guide line or the aspiration cannula. In order to avoid sample contamination, it is therefore desirable to change the test sample aspiration cannula before the next measurement.

The purpose of the present invention therefore is to provide an arrangement such as that described hereinabove, which as been modified so that the leakage of the sample fluid from the aspiration cannula is avoided and that a faster and more intensive cleaning of the flow channel is achieved.

SUMMARY OF THE INVENTION

The foregoing task is achieved therein that in a measuring device for determination of the activity or the concentration of ions in solution comprising a flow channel having a reference electrode and at least one measuring electrode, said flow channel having a first end and a second end; a first line connecting said first end of said flow channel to at least one calibrating liquid container through first valve means, a first pumping means interposed in said first line between said first valve means and said first end of said flow channel; a discharge line connected to said first line adjacent said first end of said flow channel said discharge line having second pumping means; a sample feed line connected to said second end of said flow channel for providing a sample to said flow channel; first and second sensors arranged in said first and second ends of said flow channel, respectively, for detecting the flow fronts of liquids, said sensors being capable of discriminating between the presence and absence of liquids and control means coupled to said sensors, pumping means, and valve means for controlling said pumping means and valve means the improvement comprising a connection line branching off from said exit line of aid second pump said connection line exiting into said flow channel in the vicinity of said first exit, said connecting line, being provided with a first valve and in said exit line, between said juncture of said lines and at mixing point and the point of connection of connection line to said exit line, a second valve being provided.

These two valves can be constructed as a combined valve. Such a construction enables the provision of an additional air valve which facilitates the intensive cleaning of the electrode water/air segments during the wash phase. The provision of such air valves has been previously disclosed in DE OS 3416595, the disclosure of which is incorporated herein by reference.

The washing, calibration and measurement steps can be carried out utilizing the following arrangement.

The solution to be measured is provided by the aspiration cannula which dips into the sample fluid. The sample is sucked in by means of the pump which is provided to the discharge line. The valve in the discharge line remains closed and the valve in the connecting line is briefly opened. This causes the sample fluid to flow through the aspiration cannula into the connecting line and the aspiration cannula is washed by this means. Subsequently, the valve in the connection line is closed and the valve in the discharge line is opened. This causes the sample fluid to flow into the flow channel of the electrode unit. After the channel is filled, the requisite parameters are measured by means of the electrodes and the measuring arrangements attached thereto. After completion of the measurement, the sample fluid is pumped off over the discharge line into the discharge container.

Subsequently, the electrodes are washed with two different fluids. This is achieved as follows. The valve in the discharge line is closed, the valve in the connecting line is opened and a first calibration fluid is caused to flow through the flow channel of the electrode entity by means of the first pump and from there over the aspiration cannula by means of the second pump through the connecting line into the discharge line and then into the discharge container. In view of the stronger pumping action of the second pump, an under pressure results in the interior of the aspiration cannula adaptor and the aspiration cannula so that fluid exiting from the aspiration cannula is immediately removed. The same washing step is thereafter carried out with a second calibration solution. After this washing step, the still partially contaminated calibration fluid must be removed from the flow channel of the electrode entity. In this step, the valve in the connecting line is closed and the valve in the discharge line is opened. By means of the double action pump, the calibration fluid is pumped up to the mixing point. At the same time, the pump segment in the exit line pumps off the calibration fluid through the exit line. This causes an under pressure in the flow channel of the electrode entity which in turn has the result that the fluid remaining therein is sucked off. During this pumping stage to remove residual fluid from the flow channel, air flows through the sampling aspiration cannula.

Where, additionally, an air valve is provided in the dosage line, then the possibility exists that the calibration fluid can be sucked out over the connection line, since the air can also stream through the dosage line. The air which is pumped through the flow channel, causes the liquid remaining in the aspiration cannula adaptor to be forced out and to be pumped off through the connection line.

THe subsequent filling of the flow channel of the electrode entity with clean calibration fluid, occurs when the valve in the exit line is closed and the valve in the connecting line is opened. The provision of calibration fluid continues until the flow channel in the measuring arrangement is completely filled. Thereafter, the pump is switched off and the measurement of the calibration fluid carried out. The suction removal of the calibration fluid then occurs again when the pump is activated, the valve in the discharge line is opened and the valve in the connection line is closed. There then again follows the washing step, as well as the provision of the further calibration fluid. Measurement and suction then follow in the same manner.

The arrangement of the present invention has the advantage that by provision of the connecting line, the leakage of sample or dosing fluid from the suction aspiration cannula is avoided. This step proceeds independently of variations in the efficiency of the pump. By the provision of the connecting line, a continuous connection is achieved between the containers with the calibration fluid over the electrode entity to the discharge container. The wash fluid can thus be readily pumped through the flow channel of the electrode entity without altering the flow direction during the cleaning step, which change of direction occurred in the processes of the known art. This gives rise to a faster and more intensive cleaning of the electrode channel.

There is a further advantage in that the dosage times are shortened. In the known procedures, the dosage step had to be completed exactly when the flow channel was filled with calibration fluid. This is no longer necessary since the excess calibration fluid moves into the connecting line and no longer leaks from the aspiration cannula.

DETAILED DESCRIPTION OF THE PREFERRED EMBODIMENTS

Figure 1:
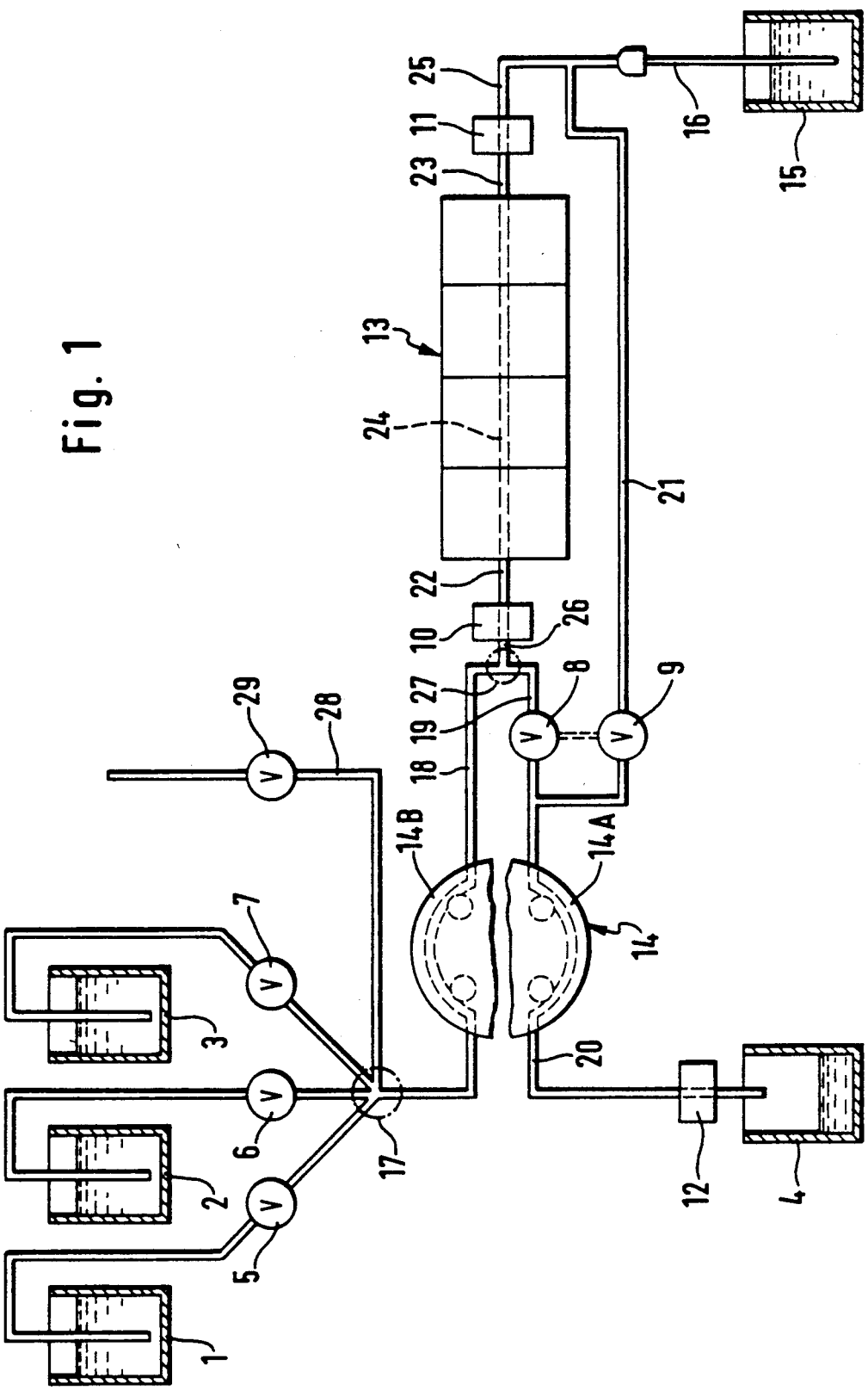
FIG. 1 is a schematic representation of a first embodiment of the invention.

FIG. 1 shows the electrode block 13 which is penetrated by flow channel 24. The flow channel 24 comprises a first end 22 and a second end 23, which are connected to a first (dosage) line 26 and a second line 25. Line 25 serves as a sample load line and is connected at end 23 with aspiration cannula 16 which dips into the sample container 15. The combined line 18 and 26 forms the dosage line for the provision of calibration fluid into the flow channel 24. The dosage line (18 and 26) is connected with the individual calibration fluid containers 1, 2 and 3 over mixing points (26) and (17). In line segment 18, there is provided a first pump 14 which is advantageously provided as a peristaltic pump.

In the illustration, pump 14 operates as a two-part pump. Pump part 14A causing anti-clockwise flow in line water segment 20 and part 14B causing anti-clockwise flow in dosage line segment 18. In the illustrated modification, part 14B serves to lead the calibration fluid through line 18 and part 14A serves to discharge the fluid into discharge container 4.

Line 20, in combination with line segment 19, forms the discharge or water line, which is connected with the second (sample) line 25 via connecting line 21. These lines have an open connection to aspiration cannula 16. Both valves can be connected and operated as a combined valve with the opening and closing means so oriented that one line is always open and the other line is always closed. This is indicated in the figure by the "dashed" line.

In order to monitor the filling of the lines, there are provided first, second and third sensors 10, 11 and 12. In order to carry out the measurement of the sample fluid, the sample is sucked out of sample container (15) through aspiration cannula 16 by means of pump 14 (suitably 14A). Thereafter, valve 8 is closed and valve 9 is opened. This causes the sample to flow through connecting line 21, whereby the aspiration cannula 16 is cleansed. Subsequently, valve 9 is closed and valve 8 is opened. The test fluid is then sucked up to mixing point 27 and first and second sensors 10 and 11 ensure the correct filling of the flow channel 24. WHen the column of liquid reaches sensor 10, the pump operates for a short but predetermined time to ensure that the residue of the calibration fluid in the fluid channel 24 is entirely removed from the measurement zone and into the waste line 19. Thereupon follow the measurement of the desired parameters during which stage the pump 14 is switched off by means of a control arrangement which is not illustrated.

After completion of the measurement of the desired parameters, valve 8 is opened and pump 14 is activated for a sufficient length of time, until the sample has been totally pumped through the discharge line 19 and 20 into the discharge container 4. There then proceeds the washing step in which the calibration fluid from containers 1, 2 or 3, or air via aeration access 28, is provided to the system. In the operation of this step, valves 5, 6 or 7 are opened and the calibration fluid flows over lines 18 and 26 to flow channel 24. For this purpose, valve 8 is closed and valve 9 is opened. The calibration fluid thus passes through flow channel 24 over the sample line 25 and the aspiration cannula adaptor 16, which are washed through at the same time and then passes through connecting line 21 over line 20, directly into the discharge container 4. Because of the differential pump action of pump 14 in discharge line 20, which is achieved by a different cross-section in comparison to the dosage line 18, an under pressure is provided inside the aspiration cannula adaptor and the aspiration cannula 16, so that the aspiration cannula itself is ultimately pumped clear of the fluid which it contains.

The washing arrangement can be improved even further in that upon occasion, air segments are introduced into line 18. In order to achieve this result, a further air line with an air valve (not illustrated) is provided at mixing point 17. After the conclusion of the ashing step, valve 9 is closed and valve 8 is opened. This causes calibration fluid to flow through line 18 but, because of the action of the first pump segment (14A), calibration fluid is again pumped off through line 20, which leads to an under pressure in flow channel 24 which, by this means, becomes emptied. Thereupon valve 8 is again closed and valve 9 is opened. In this manner, calibration fluid is led to the electrode entity until flow channel 24 is entirely filled. After sensors 10 and 11 indicate the correct level of filling in the flow channel 24, pump 14 is deactivated and the measuring of the calibration fluid is carried out. The subsequent suction clearing and washing then follow in the manner described above. There follows a further calibration step with a second calibration fluid. Thereafter, a further sample measurement may be carried out.

Figure 2:
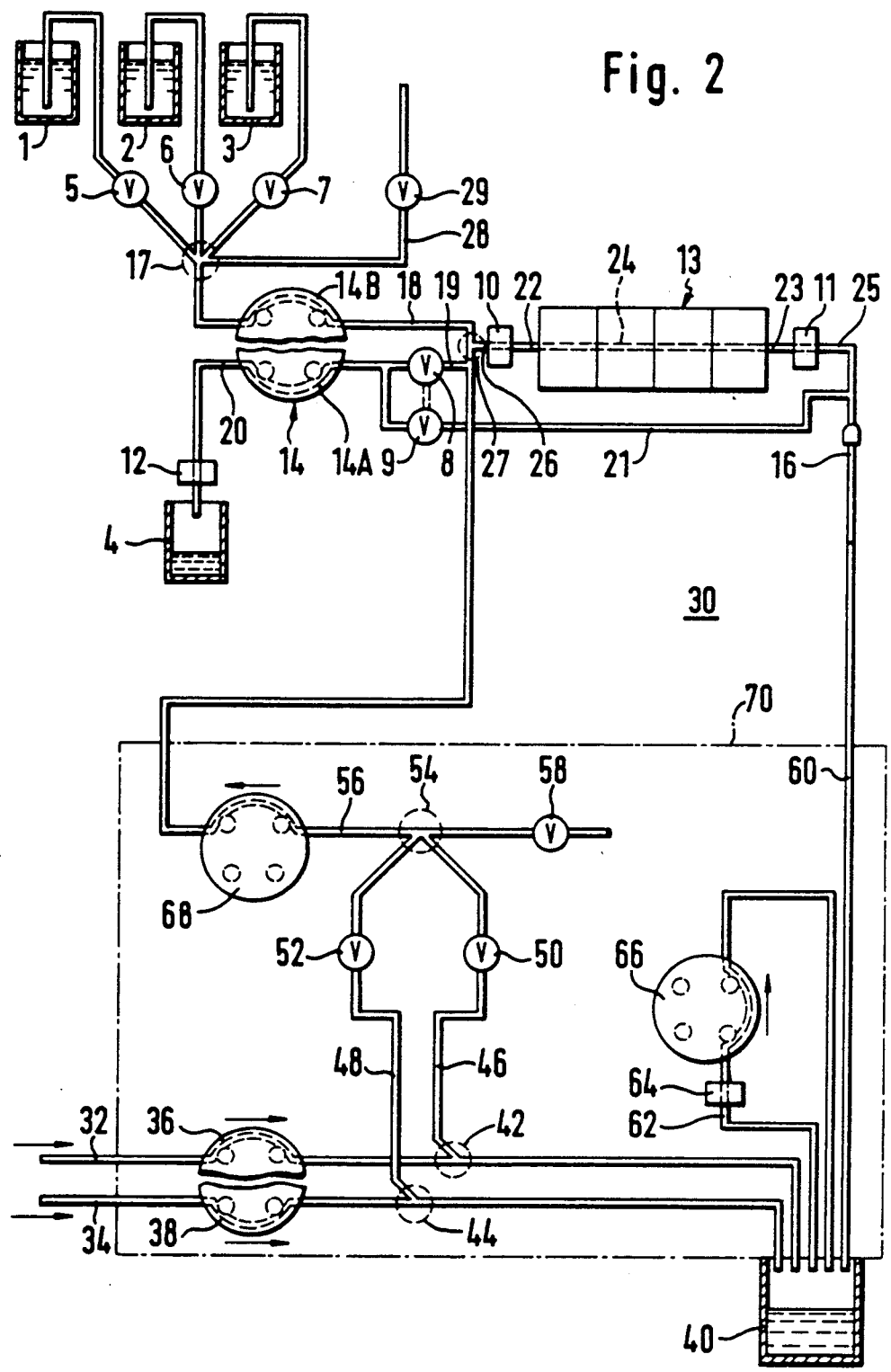
FIG. 2 is a schematic representation of a further embodiment of the invention.

FIG. 2 illustrates a second embodiment 30 of the apparatus of the present invention, wherein the same parts carry the same item numbers as in FIG. 1. This embodiment enables the arrangement to be carried out as a quasi continuous measuring process.

In this embodiment, there is provided a first sample line 32 and a second sample line 34 to which, respectively, a pump 36 and a pump 38 are provided and said lines connected with a discharge container 40. Downstream from pumps 36 and 38, branching off from first sample line 32 and second sample line 34, at mixing points 42 and 44 respectively, are a first and a second branch line 46 and 48 respectively, which contain closing means, suitably valves 50 and 52 respectively. Downstream from said valves 50 and 52, the branch lines 46 and 48 exit into a forwarding line 56 at junction point 54. Said forwarding line 56 itself exits into line 19 upstream of valve 8 and the other end thereof is provided with a further valve 58.

As will be seen from FIG. 2, in addition to sample lines 32 and 34, air line 60 which is connected to aspiration cannula 16 also is connected to discharge container 40. Finally, a further filling level detector line 62 is provided which is so laid in a loop, that both ends thereof are placed in the discharge container, so that by means of a filling level detector 64, pump 66 is activated for filling line 62, so that the filling level of the discharge container 40 may be measured. Furthermore, downstream from the junction point 54 in forwarding line 56, there is provided a forwarding pump 58 which, when activated, transports a smaller volume than the sample forwarding pumps 36 and 38.

As may be seen from FIG. 2, only the forwarding lines 32 and 34 and their corresponding pumps 36 and 38, branch pumps 42 and 44, branch lines 46 and 48 and valves 50 and 52 are shown. In accordance with the principals of the present invention, a plurality of lines may be provided using nevertheless, only a single inlet line. Furthermore, it is advantageous when, as shown in phantom in FIG. 2, a plurality of lines which are connected with pumps 36, 38, 66 and 68, these pumps are taken up in a single cassette or container, so that the location of the entire lead system on a (not illustrated) mounting plate of pumps 36, 38, 66 and 68 may be achieved.

A similar arrangement, as illustrated in FIG. 2, is shown in EP A 166920, whose disclosure is incorporated herein by reference.

The arrangement 30 shown in FIG. 2, may be utilized to carry out a quasi continuous measuring processing in the following manner.

The sample is provided over one of the sample lines 32 or 34 in a continuous manner assisted by pumps 36 and 38 through to the discharge container 40. In order to measure a sample, for example, a sample supplied through line 32, valve 50 is opened. The action of pump 68 while valve 8 is closed supplies the sample to the electrode block until the electrodes 10 and 11 provide a detection signal. Then pump 68 is deactivated.

The first and possibly contaminated part of the sample is delivered to the discharge container 4 by a short activation of pump 14 and the opening of valves 8 and then 9.

Thereafter, the sample in the electrode block 13 is removed by activation of pump 14 and followed by opening of valves 8 and 9. Thus the first dosage of the sample serves to wash the electrode block. Thereafter, the sample is resupplied and as described hereinabove, provided to the electrode block whereupon the measuring step follows. Subsequently, the sample is forwarded to the discharge container 4 in the manner previously described.

Thereupon follows the equally previously described calibration with the appropriate calibration fluid.

In yet another embodiment, the forwarding line of 56 can be pumped dry wherein the ventilation valve 58 is opened and the forwarding pump 68 is activated. At the same time pump 14 is activated and valve 8 is opened.

According to the measuring frequency chosen, there is a time interval wherein the measuring channel is empty. During this time, the sample pumps 36 and 38 are set to run at a lower speed and valves 50 and 52 are closed and pump 68 taken out of operation. Before the samples next to be measured are pumped into the electrode block, pumps 36 and 38 are advantageously moved to operate at a higher pumping speed so that the actual sample is, in fact, supplied.

The aeration tube 60 is only supplied to aspiration cannula 16 for safety reasons and can in fact, be dispensed with particularly when a single sample should be supplied to aspiration cannula 16 so that, in fact, the system operates in accordance with that illustrated in FIG. 1. In any event, the air lead 60 should be filled with air so that the measuring channel is not influenced by pressure variations. Thus no pressure operates upon the electrodes 13 during the measuring step.

After each of the quasi continual measurements, as mentioned hereinabove, a calibration may take place. It should be noted that there is no warming of the electrode block 13 because of the sample, since between the measurements there is a substantial lapse of time in which the measuring channel remains empty.

I claim:
1. In a measuring device for determination of the activity or the concentration of ions in solution comprising;

a flow channel having a reference electrode and at least one measuring electrode, said flow channel having a first end and a second end;

a first line connecting said first end of said flow channel to at least one calibrating liquid container through first valve means;

first pumping means interpose din said first line between said first valve means and said first end of said flow channel a discharge line connected to said first line adjacent said first end of said flow channel, said discharge line having second pumping means;

a sample feed line connected to said second end of said flow channel for providing a sample to said flow channel first and second sensors arranged in said first and second ends of said flow channel, respectively, for detecting the flowing fronts of liquids, said sensors being capable of discriminating between the presence and absence of liquids; and control means coupled to said sensors, pumping means, and valve means for controlling said pumping means and valve means;

the improvement comprising a connection line branching off from said exit line of said second pump, said connection line exiting into said flow channel in the vicinity of said second end, said connecting line, being provided with a first valve and in said exit line, between the juncture of said lines and at mixing point and the point of connection of connection line to said exit line, a second valve is provided.

2. In a measuring arrangement in accordance with claim said second end exit of the flow channel being connected with said sample lien the distal end whereof being provided with an aspiration cannula.

3. In a measuring arrangement in accordance with claim 2, said first and second valves being provided as a combined valve arranged to operate in mutually opposed settings.

4. In a measuring arrangement in accordance with claim 3, the distal ends of both said test line and said connecting line exiting into the same aspiration cannula.

5. In a measuring arrangement according to claim 1, said discharge line being connected with at least one sample line through a forwarding line and at least one branch line over at least one branch point, said sample line being provided with at least one pump the distal end thereof being connected with discharge container, said forwarding line being provided with a forwarding pump.

6. In a measuring arrangement according to claim 5, at least one valve being provided in said branch line said valve being open in the forwarding position.

7. In a measuring arrangement in accordance with claims 5, the distal end of said forwarding line being provided with a clearing valve, said valve being open during the clearing step.

8. In a measuring arrangement in accordance with claim 7, said discharge container being provided with a full level signaling means.

* * * * *